(12) United States Patent
Chen

(10) Patent No.: US 7,063,957 B2
(45) Date of Patent: Jun. 20, 2006

(54) **METHODS FOR PRODUCTION OF ASTAXANTHIN FROM THE GREEN MICROALGAE *CHLORELLA* IN DARK-HETEROTROPHIC CULTURES**

(75) Inventor: Feng Chen, Hong Kong (CN)

(73) Assignee: The University of Hong Kong, Hong Kong (HK)

( * ) Notice: Subject to any disclaimer, the term of this patent is extended or adjusted under 35 U.S.C. 154(b) by 51 days.

(21) Appl. No.: 10/809,862

(22) Filed: Mar. 26, 2004

(65) Prior Publication Data

US 2005/0214897 A1    Sep. 29, 2005

(51) Int. Cl.
*C12P 23/00* (2006.01)
*C12P 1/00* (2006.01)
*C12N 1/12* (2006.01)

(52) U.S. Cl. .................. 435/67; 435/41; 435/257.3

(58) Field of Classification Search .................. 435/67, 435/41
See application file for complete search history.

(56) References Cited

U.S. PATENT DOCUMENTS 3,280,502 A * 10/1966 Farrow et al. ................ 435/67

OTHER PUBLICATIONS

Ip, P.-F., et al. 2004. Enhanced production of astaxanthin by the green microalga *Chlorella zofingiensis* in mixotrophic culture. Process Biochemistry 39: 1761-1766. Available online Nov. 4, 2003.*

* cited by examiner

*Primary Examiner*—Sandra E. Saucier
*Assistant Examiner*—Lora E Barnhart
(74) *Attorney, Agent, or Firm*—Dickstein, Shapiro, Morin & Oshinsky, LLP.

(57) ABSTRACT

A method for producing the high-value ketocarotenoid astaxanthin by the green microalga *Chlorella zofingiensis* in dark-heterotrophic cultures shows excellent growth and high-yield astaxanthin production on glucose-supplemented media in the dark. The specific growth rate and astaxanthin yield can be as high as 0.031 $h^{-1}$, and 10.3 mg $l^{-1}$, respectively, which are the highest so far reported in heterotrophic algal cultures. The light-independent astaxanthin-producing ability of *Chlorella zofingiensis* can be employed for commercial production of astaxanthin using industrial fermenters.

16 Claims, 3 Drawing Sheets

Canthaxanthin

Adonixanthin

Astaxanthin

METHODS FOR PRODUCTION OF ASTAXANTHIN FROM THE GREEN MICROALGAE *CHLORELLA* IN DARK-HETEROTROPHIC CULTURES

BACKGROUND OF THE INVENTION

The green algae *Chlorella* has attracted considerable interest for commercial production of functional foods. Examples include polyunsaturated fatty acids by *Chlorella sorokiniana* [Chen F and Johns M R, 1991] and lutein by *Chlorella protothecoides* [Shi X M et al., 2002]. More recently, *Chlorella zofingiensis* has been proposed as a promising producer for the high-value carotenoid pigment, astaxanthin [Orosa M et al., 2000; Ip, P F et al., 2004]. Astaxanthin (3,3'-dihydroxy-β,β'-carotene-4,4'-dione) (FIG. 1) has been used as feed additives to elicit the pinkish-red color to the flesh of aquatic animals, and to improve their growth and survival in the aquaculture industry [Lorenz R T and Cysewski G R 2000; Pan C H et al., 2001]. Recent studies have also shown that astaxanthin is a potent antioxidant and is effective for the prevention of certain cancers [Tanaka T et al., 1995; Nishino H et al., 1999; Lyons N M and O'Brien N M, 2002]. The annual worldwide market for astaxanthin has been estimated at US$200 million [Lorenz R T and Cysewski G R 2000]. However, astaxanthin is expensive and sells for approximately US$2,500 per kg.

Light has been employed for enhancing astaxanthin formation in algal cultures [Orosa M et al., 2000; Hata N et al., 2001; Zhang D H and Lee Y K, 2001]. However, the attenuated light absorption caused by mutual shading of cells in large-scale cultures severely affects the productivity and quality of algal biomass and products [Chen, 1996; Zaslavskaia L A et al., 2001]. For instance, Harker et al. [1996] reported that the content of astaxanthin in a green alga *Haematococcus pluvialis* cultivated in a 30-litre photobioreactor was significantly lower than that obtained in a smaller laboratory-scale culture, indicating the insufficiency of illumination in the scaled-up culture system. The high cost of lighting is another problem hindering the commercialization of microalgal products [Borowitzka M A, 1999]. To overcome such a problem, a heterotrophic culture approach may be considered because in heterotrophic culture, light is not needed and the organic substrate serves as the sole carbon and energy source [Chen, 1996; Zaslavskaia L A et al., 2001]. Although heterotrophic cultivation in most *Chlorella* species has been achieved [Chen F and Johns M R, 1991; Shi X M et al., 2002; Endo H et al., 1977], no literature is available concerning the production of astaxanthin by growing *C. zofingiensis* in the dark.

A high carbon to nitrogen (C/N) has been suggested to induce astaxanthin biosynthesis because nitrogen limitation in the presence of excess organic carbon substrates such as acetate and glucose has proved effective in enhancing astaxanthin production in mixotrophic cultures [Ip P F et al., 2004; Kakizono T et al., 1992]. While there may be involvement of the additional carbon in the form of $CO_2$ in the photosynthetic process of mixotrophic cultures, $CO_2$ is not involved in the biosynthesis in heterotrophic culture such as the biosynthesis of astaxanthin. Nevertheless, it has now been found that the production of astaxanthin and other carotenoids by *Chlorella*, especially *C. zofingiensis*, in dark-heterotrophic culture can be enhanced by increasing the initial C/N ratios in the medium.

SUMMARY OF THE INVENTION

This present invention is based in part on the surprising discovery that the green microalgae *Chlorella*, especially *Chlorella zofingiensis*, can be grown on glucose (or other carbon source) supplemented medium in the dark, and at the same time produce large quantities of intracellular secondary carotenoids such as astaxanthin, canthaxanthin or adonixanthin or their derivatives. This discovery enables the production of the carotenoid by the green microalgae *Chlorella* to be achieved on a large scale using industrial fermenters. In one example, the microalga *Chlorella zofingiensis* exhibits excellent growth and high-yield astaxanthin production in batch culture. The maximum specific growth rate and astaxanthin yield achieved are 0.031 $h^{-1}$ and 10.3 mg $l^{-1}$, respectively, which are the highest so far reported in heterotrophic algal cultures. The present invention also shows that the initial carbon/nitrogen (C/N) ratio in the medium has significant impact on the biosynthesis of secondary carotenoids (including astaxanthin) in the algal cell; enhanced formation of secondary carotenoids is found in the medium with a high C/N ratio of 180. The light-independent astaxanthin-producing ability of *C. zofingiensis* suggests that the green microalga *Chlorella zofingiensis* can be employed for commercial production of astaxanthin and related carotenoids.

DETAILED DESCRIPTION

Figure 1:
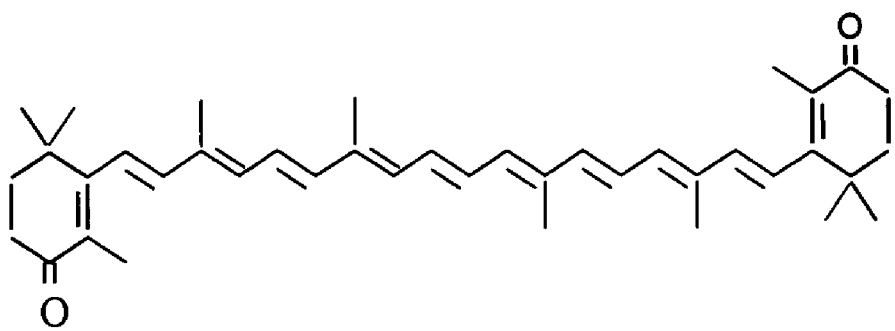
FIG. 1 shows the chemical structures of canthaxanthin, adonixanthin and astaxanthin.
Figure 1:
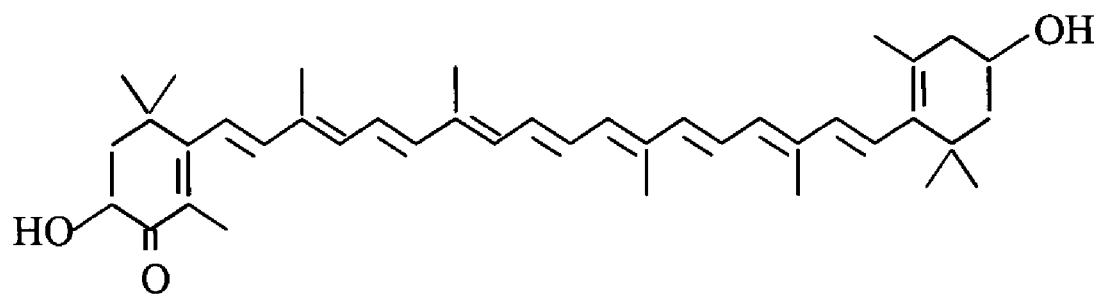
Figure 1:
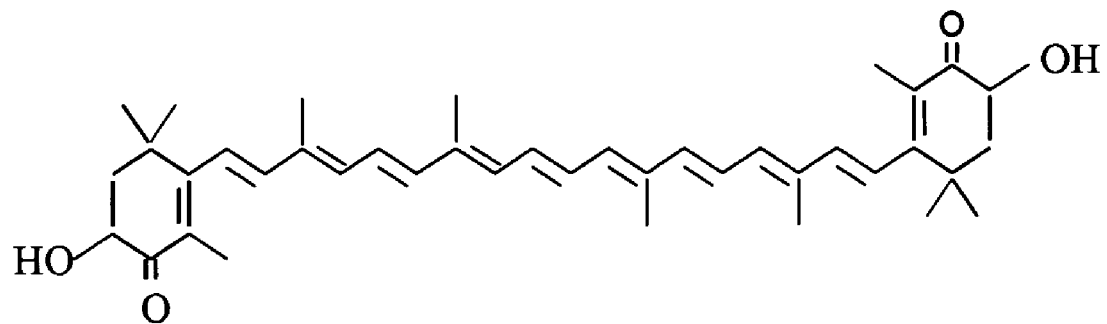

In accordance with the present invention, any known process for the production of carotenoids, especially astaxanthin, by *Chlorella* is enhanced by conducting the process in heterotrophic culture, in the dark, when the carbon source quantity is increased. Increasing the carbon source quantity, in this connection, means establishing a carbon/nitrogen ratio of at least about 5, and preferably at least about 90. The C/N ratio in the media heretofore employed did not exceed about 18. Any known carbon source such as glucose, acetate, lactose, fructose, sucrose, maltose, mannitol or mannitose can be employed for this purpose although the use of glucose is presently preferred.

The invention is demonstrated in the following examples.

Methods

The Microalga and Culture Conditions

The green microalga, *Chlorella zofingiensis* (ATCC 30412) was obtained from American Type Culture Collection (ATCC, Rockville, USA). The alga was maintained in the modified Bristol's medium (referred to as CZ-M1) which consisted of (per litre): 0.75 g $NaNO_3$; 0.175 g $KH_2PO_4$; 0.075 g $K_2HPO_4$; 0.075 g $MgSO_4.7H_2O$; 0.025 g $CaCl_2.2H_2O$; 0.025 g NaCl; 5 mg $FeCl_3.6H_2O$; 0.287 mg $ZnSO_4.7H_2O$; 0.169 mg $MnSO_4.H_2O$; 0.061 mg $H_3BO_3$; 0.0025 mg $CuSO_4.5H_2O$; and 0.00124 mg $(NH_4)_6Mo_7O_{24}.7H_2O$. The culture (4 days old) grown in the medium supplemented with 10 g $l^{-1}$ glucose and illuminated with florescence light at 90 μmol $m^{-2}$ $s^{-1}$ at the flask surface was used as inoculum. Different concentrations of glucose (5–60 g $l^{-1}$) were added to 250-ml Erlenmeyer flasks, each containing 100 ml medium. To examine the effect of the initial C/N ratios in the medium on astaxanthin formation in the algal cells, glucose concentrations were fixed at 10 g $l^{-1}$, 30 g $l^{-1}$ and 50 g $l^{-1}$ and the initial C/N ratios were adjusted to 18, 55, 90 and 180 by varying the concentrations of nitrate. All media in the flasks were adjusted to pH 6.5 prior to autoclaving at 121° C. for 20 min. An inoculum of 10% (by volume, average cell concentration of 0.5 g $l^{-1}$ dry weight) was inoculated rapidly into each flask under dim light. The cultures were then incubated at 30° C. with orbital shaking at 130 rpm under darkness.

Determination of Glucose, Protein, Cell Dry Weight Concentration and Specific Growth Rate The culture fluid (3 ml) was centrifuged at 3,800×g for 3 min. Glucose concentration in the supernatant was determined according to Miller [Miller G L, 1959]. The pellet was re-suspended in distilled water and filtered through a pre-dried Whatman GF/C filter paper (1.2 μm pore size). The algal cells on the filter paper discs were dried at 70° C. in a vacuum oven until constant weight and were cooled down to room temperature in a desiccator before weighing. Specific growth rate (μ) at the exponential phase was calculated according to the equation $\mu=(\ln X_2-\ln X_1)/(t_2-t_1)$, where $X_2$ and $X_1$ are the dry cell weight concentration (g $l^{-1}$) at time $t_2$ and $t_1$, respectively. The protein content in the algal cells was determined by the dye-binding method as described by Bradford [Bradford M M, 1976].

Determination of Pigments

Cell pellets (2 weeks old) were obtained by centrifuging the culture samples at 3800×g at 4° C. for 3 min and were dried in a DW3 freeze-drier (Heto Dry Winner, Denmark). The freeze-dried cells were ground with the extraction solvent containing methanol/dichloromethane (3:1) under nitrogen until the cells became colourless. The pigment dissolved in the extraction solvent was collected by centrifugation at 20,800×g at 4° C. for 1 min, which was subsequently dried by nitrogen gas. Then, 1 ml of the extraction solvent was added to the dried preparation and filtered through a 0.22 μm Millipore organic membrane prior to HPLC analysis. The whole process was carried out in darkness.

For determination of pigment contents by HPLC, the chemical standards of astaxanthin, β-carotene, lutein, and chlorophylls α and β were purchased from Sigma Chemical Co. (St. Louis, Mo., USA). Canthaxanthin was bought from Dr. Ehrenstorfer GmbH (Augsburg, Germany). HPLC-grade acetonitrile, dichloromethane and methanol were obtained from BDH Laboratory Supplies (Poole, UK). The pigment concentrations were determined according to the method of Yuan et al. [2002]. Briefly, the extracted pigments (20 μl aliquots) were separated and analysed on an HPLC system (Waters, Milford, M A. USA) equipped with two 510 pumps and a 996 photodiode array detector, using a Beckman Ultrasphere $C_{18}$ (5 μm; 250×4.6 mm) column. The mobile phase consisted of solvent A (dichloromethane/methanol/acetonitrile/water, 5:85:5.5:4.5 by volume) and solvent B (dichloromethane/methanol/acetonitrile/water, 25:28:42.5:4.5 by volume). The gradient used was: 0% B for 8 min, followed by a linear gradient of 0–100% B for 6 min and then 100% B for 40 min. The flow rate was 1.0 ml $min^{-1}$. The absorption spectra of the pigments were shown between 250 and 700 nm. Peaks were measured at a wavelength of 480 nm to facilitate the detection of chlorophylls and carotenoids.

Results

Figure 2:
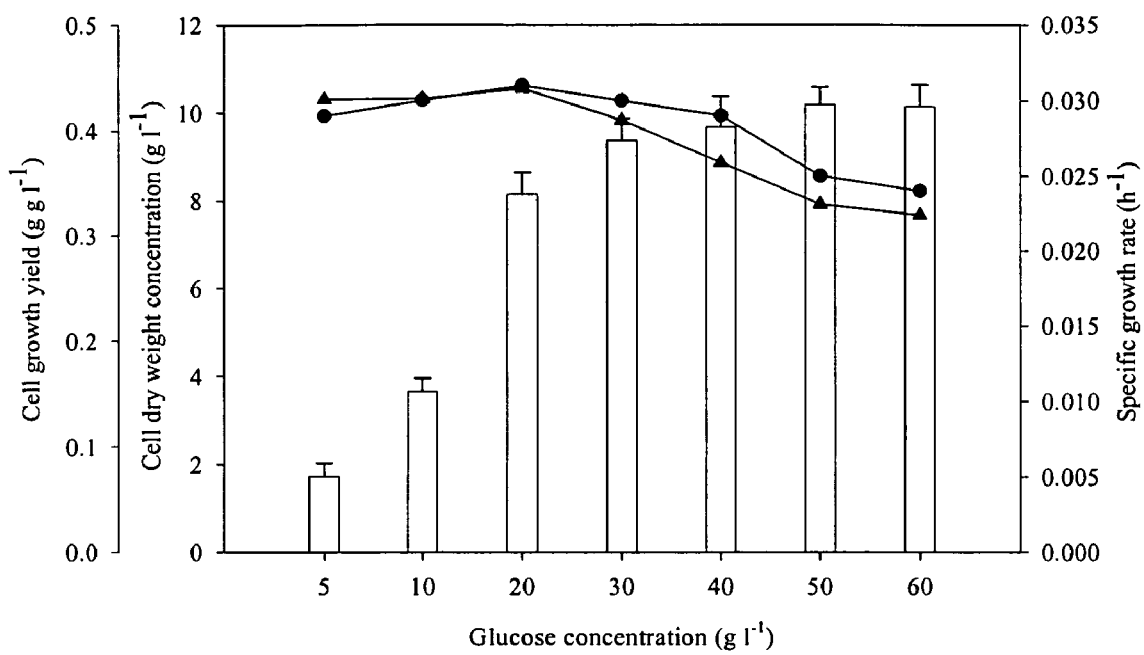
FIG. 2 plots the heterotrophic growth of *C. zofingiensis* at various glucose concentrations. Maximum cell dry weight concentration (■), specific growth rate (●) and cell growth yield (▲). The cell growth yield (Y) is calculated according to Y=ΔX/ΔS, where ΔX is the biomass increased and ΔS is the glucose consumed.

Heterotrophic growth of *C. zofingiensis* in the medium containing 5–60 g $l^{-1}$ glucose is achieved and the results are presented in FIG. 2. The alga exhibits the highest specific growth rate (0.031 $h^{-1}$) and the highest growth yield (0.44 g $g^{-1}$) at a glucose concentration of 20 g $l^{-1}$. The highest biomass yield (10.2 g $l^{-1}$) obtained, however, is found at glucose concentrations of 50–60 g $l^{-1}$ (FIG. 2).

In the absence of light, the use of an appropriate amount of the carbon source is crucial for attaining high biomass yield in algal culture. In the present example, glucose is used to support the algal growth and only a slight decrease in the specific growth rate and cell growth yield is found with increasing substrate concentrations up to 60 g $l^{-1}$ (FIG. 2) demonstrating that glucose is a suitable carbon source for heterotrophic cultivation of *C. zofingiensis*. Table 1 below summarizes astaxanthin content and astaxanthin yield of *C. zofingiensis* in the heterotrophic batch cultures.

TABLE 1

Heterotrophic production of astaxanthin by *Chlorella zofingiensis* at various glucose concentrations*

| Glucose concentration (g $l^{-1}$) | Astaxanthin content (mg $g^{-1}$) | Astaxanthin yield (mg $l^{-1}$) |
|---|---|---|
| 5 | 0.44 ± 0.02 | 0.76 ± 0.3 |
| 10 | 0.65 ± 0.03 | 2.37 ± 0.3 |
| 20 | 0.72 ± 0.04 | 5.87 ± 0.5 |
| 30 | 0.90 ± 0.03 | 8.50 ± 0.5 |
| 40 | 0.97 ± 0.03 | 9.39 ± 0.7 |
| 50 | 1.01 ± 0.04 | 10.30 ± 0.4 |
| 60 | 0.95 ± 0.04 | 9.64 ± 0.5 |

*Data are expressed as mean ± standard deviation of three replicates.

The alga produces astaxanthin at all glucose concentrations. The cellular astaxanthin content is increased considerably with increasing glucose supply; the highest content and yield of astaxanthin are 1.01 mg $g^{-1}$ and 10.3 mg $l^{-1}$, respectively, at 50 g $l^{-1}$ glucose. Astaxanthin formation by *H. pluvialis* grown in the dark was reported [Hata N et al., 2001; Kobayashi M et al., 1992; 1997]. However, the amount of astaxanthin produced was merely confined to 9 mg $l^{-1}$ even after the induction by salt stress [Kobayashi M et al., 1997]. In the present example, the maximum yield of astaxanthin is 10.3 mg $l^{-1}$ at 50 g $l^{-1}$ glucose, which is the highest compared to other organisms in heterotrophic cultures (see Table 2 below).

TABLE 2

Comparison of astaxanthin production potential by
various microorganisms in heterotrophic batch cultures

| Organisms (carbon source) | Specific growth rate ($h^{-1}$) | Growth yield ($g\ g^{-1}$) | Maximum biomass concentration ($g\ l^{-1}$) | Astaxanthin content ($mg\ g^{-1}$) | Astaxanthin yield ($mg\ l^{-1}$) | References |
|---|---|---|---|---|---|---|
| *Chlorella zofingiensis* (30 g $l^{-1}$ glucose) | 0.029 | 0.41 | 9.44 | 0.9 | 8.5 | Present invention |
| *Haematococcus pluvialis* (22.5 mM acetate) | 0.01 | 0.42 | 0.54 | 5.8 | 3.1 | Kobayashi et al. (1992); Hata et al. (2001) |
| *Phaffia rhodozyma* (60 g $l^{-1}$ glucose) | 0.084 | 0.17 | 9.90 | 0.2 | 2.0 | Yamane et al. (1997) |

Furthermore, the average specific growth rate (0.028 $h^{-1}$) of *C. zofingiensis* obtained in this example is remarkably higher than that of *H. pluvialis* (approximately 0.01 $h^{-1}$) in heterotrophic cultures [Hata N et al., 2001; Kobayashi M et al., 1992]. These results clearly suggests that *C. zofingiensis* is superior to *H. pluvialis* in terms of heterotrophic production of astaxanthin.

Figure 3:
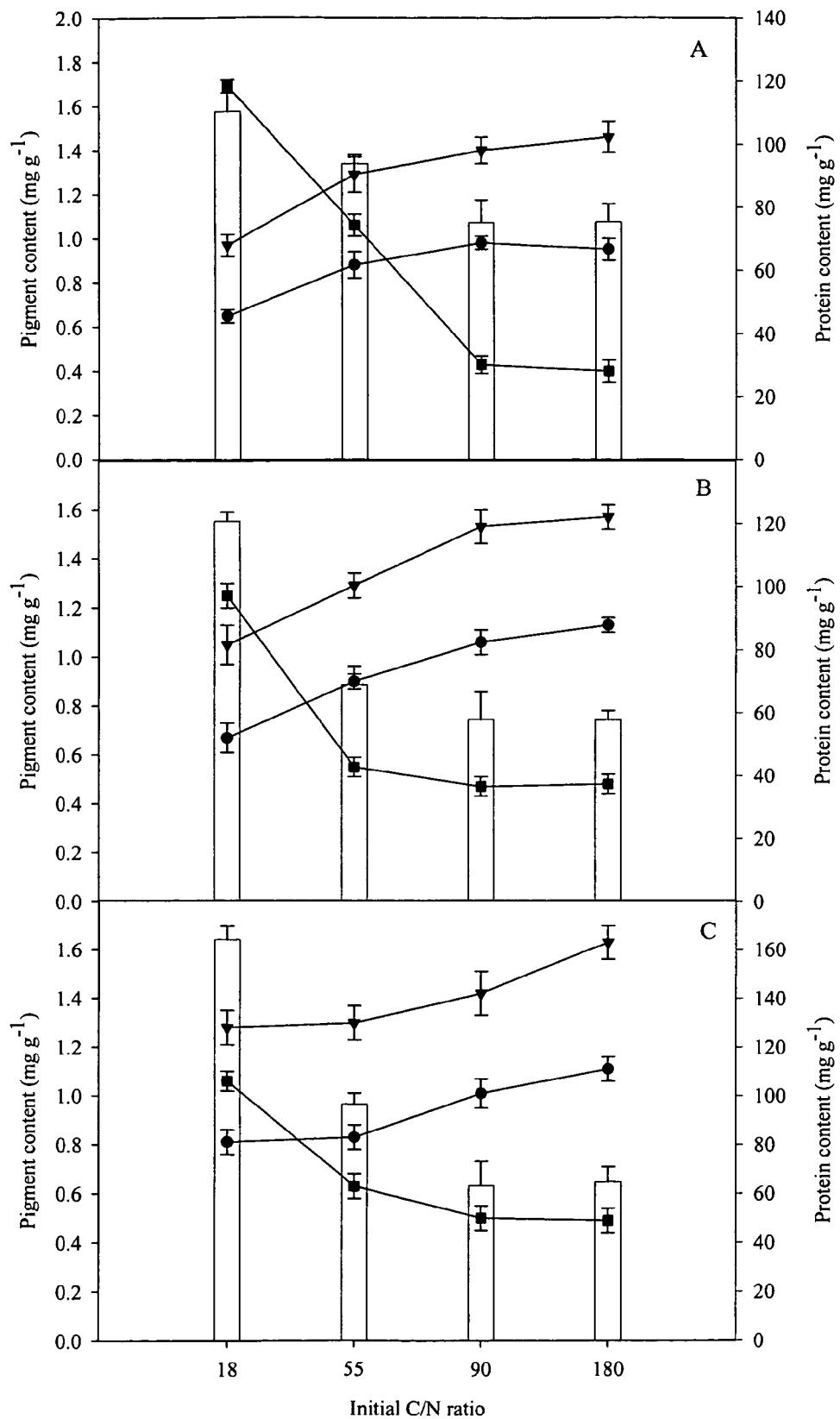
FIG. 3 shows the influence of initial C/N ratio on protein, chlorophylls (a and b), total secondary carotenoids (i.e., astaxanthin, canthaxanthin and adonixanthin) and astaxanthin contents in *C. zofingiensis*. Glucose concentrations were fixed at (A) 10 g $l^{-1}$, (B) 30 g $l^{-1}$ and (C) 50 g $l^{-1}$. Protein (■), chlorophylls (■), secondary carotenoids (▼) and astaxanthin (●).

In the light-independent cultivation system of the present invention, the compositions of organic compounds in the medium, especially carbon and nitrogen, are the main factors affecting carotenogenesis in the algal cells. FIG. 3 illustrates the influence of initial C/N ratios in the medium on the contents of protein, chlorophylls and secondary carotenoids (including astaxanthin) in *C. zofingiensis*. Glucose and nitrate are used respectively as the carbon (C) and nitrogen (N) sources in the cultures. Over the entire range of initial C/N ratios investigated, the contents of secondary carotenoids obtained at 50 g $l^{-1}$ glucose (FIG. 3C) (1.28–1.63 mg $g^{-1}$) are significantly higher than those obtained at 10 g $l^{-1}$ glucose (FIG. 3A) (0.97–1.46 mg $g^{-1}$), suggesting that glucose is essential for providing the carbon skeleton for the formation of secondary carotenoids including astaxanthin formation in the carotenoids biosynthetic pathway [Disch A et al., 1998].

Besides glucose, nitrate is another important compound governing the formation of carotenoids in *C. zofingiensis*. Although nitrate is not directly involved in the biosynthetic pathway of carotenoids, it can alter the normal cellular metabolism such as protein synthesis and hence indirectly affects the pigments formation in algae. As shown in FIG. 3, a decrease in the contents of protein and chlorophylls is observed with increasing C/N ratios in the medium. At a high C/N ratio (i.e., C/N ratio=180), nitrogen supply is comparatively low. The limitation of nitrogen leads to the reduction of primary metabolism (e.g., protein and chlorophylls syntheses), which in turn triggers the secondary metabolism such as astaxanthin biosynthesis in the alga (FIG. 3).

In conclusion, the green microalga *Chlorella zofingiensis* is demonstrated in this example to possess the ability to grow heterotrophically and synthesize astaxanthin in the dark. In addition, a high C/N ratio is found to facilitate astaxanthin formation by the alga. These results show that *C. zofingiensis* is an attractive alternative for massive production of astaxanthin, because light, a limiting factor in any photosynthetic systems, is eliminated. Furthermore, the astaxanthin-producing capacity by *C. zofingiensis* may be further enhanced through employing the high-cell density strategies, such as, fed-batch, chemostat and perfusion cultures [Shi X M et al., 2002; Chen F and Johns M R, 1996a; 1996b; Wen Z Y and Chen F, 2001; 2002; Wen Z Y et al., 2002], which are particularly suitable for heterotrophically growing microalgae.

Various changes and modifications can be made in the process of the present invention without departing from the spirit and scope thereof. The embodiments set forth above were intended to illustrate the invention but were not intended to be limiting.

The full citation of the references noted above are:

Borowitzka M A. Commercial production of microalgae: ponds, tanks, tubes and fermenters. J Biotechnol 1999; 70: 313–321.

Bradford M M. A rapid and sensitive method for the quantification of microgram quantities of protein utilizing the principle of protein-dye binding. Anal Biochem 1976; 72: 248–254.

Chen F. High cell density culture of microalgae in heterotrophic growth. Trends Biotechnol 1996; 14: 421–425.

Chen F, Johns M R. Effect of C/N ratio and aeration on the fatty acid composition of heterotrotrophic *Chlorella sorokiniana*. J Appl Phycol 1991; 3: 203–209.

Chen F, Johns M R. High cell density culture of *Chlamydomonas reinhardtii* on acetate using fed-batch and hollow-fibre cell-recycle systems. Biores Technol 1996a; 55: 103–110.

Chen F, Johns M R. Heterotrophic growth of *Chlamydononas reinhardtii* on acetate in chemostat culture. Process Biochem 1996b; 31: 601–604.

Disch A., Schwender J., Muller C., Lichtenthaler H. K., Rohmer M. Distribution of the mevalonate and glyceraldehyde phosphate/pyruvate pathways for isoprenoid biosynthesis in unicellular algae and cyanobacterium *Synechocystis* PCC 6714. Biochem J 1998; 333: 381–388.

Endo H, Hosoya H, Koibuchi T. Growth yields of *Chlorella regularis* in dark-heterotrophic continuous cultures using acetate. J Ferment Technol 1977; 55: 369–379.

Harker M, Tsavalos A J, Young A J. Autotrophic growth and carotenoid production of *Haematococcus pluvialis* in a 30 liter air-lift photobioreactor. J Ferment Bioeng 1996; 82: 113–118.

Hata N, Ogbonna J C, Hasegawa Y, Taroda H, Tanaka H. Production of astaxanthin by *Haematococcus pluvialis* in a sequential heterotrophic-photoautotrophic culture. J Appl Phycol 2001; 13: 395–402.

Ip P F, Wong K H, Chen F. Enhanced production of astaxanthin by the green microalga *Chlorella zofingiensis* in mixotrophic culture. Process Biochem 2004 (in press).

Kakizono T, Kobayahsi M, Nagai S. Effect of carbon/nitrogen ratio on encystment accompanied with astaxanthin formation in a green alga, *Haematococcus pluvialis*. J Ferment Bioeng 1992; 74: 403–405.

Kobayashi M, Kakizono T, Yamaguchi K, Nishio N, Nagai S. Growth and astaxanthin formation of *Haematococcus pluvialis* in heterotrophic and mixotrophic conditions. J Ferment Bioeng 1992; 74: 17–20.

Kobayashi M, Kurimura Y, Tsuji Y. Light-independent, astaxanthin production by the green microalga *Haematococcus pluvialis* under salt stress. Biotechnol Lett 1997; 19: 507–509.

Lorenz R T, Cysewski G R. Commercial potential for *Haematococcus* microalgae as a natural source of astaxanthin. Trends Biotechnol 2000; 18: 160–167.

Lyons N M, O'Brien N M. Modulatory effects of an algal extract containing astaxanthin on UVA-irradiated cells in culture. J Dermatol Sci 2002; 30: 73–84.

Miller G L. Use of dinitrosalicylic acid reagent for determination of reducing sugar. Anal Chem 1959; 31: 426–429.

Nishino H, Tokuda H, Satomi Y, Masuda M, Bu P, Onozuka M, Yamaguchi S, Okuda Y, Takayasu J, Tsuruta J, Okuda M, Ichiishi E, Murakoshi M, Kato T, Misawa N, Narisawa T, Takasuka N. Cancer prevention by carotenoids. Pure Appl Chem 1999; 71: 2273–2278.

Orosa M, Torres E, Fidalgo P, Abalde J. Production and analysis of secondary carotenoids in green algae. J Appl Phycol 2000; 12: 553–556.

Pan C H, Chien Y H, Cheng J H. Effect of light regime, algae in the water, and dietary astaxanthin on pigmentation, growth and survival of black tiger prawn *Panaeus monodon* post-larve. Zool Stud 2001; 40: 371–382.

Shi X M, Jiang Y, Chen F. High-yield production of lutein by the green microalga *Chlorella protothecoides* in heterotrophic fed-batch culture. Biotechnol Prog 2002; 18: 723–727.

Tanaka T, Makita H, Ohnishi M, Mori H, Satoh K, Hara A. Chemoprevention of mouse oral carcinogenesis by naturally occurring xanthophylls, astaxanthin and canthaxanthin. Cancer Res 1995; 55: 4059–4064.

Wen Z Y, Chen F. A perfusion-cell bleeding culture strategy for enhancing the productivity of eicosapentaenoic acid by *Nitzschia laevis*. Appl Microbiol Biotechnol 2001; 57: 316–322.

Wen Z Y, Chen F. Perfusion culture of the diatom *Nitzschia laevis* for ultra-high yield of eicosapentaenoic acid. Process Biochem 2002; 38: 523–529.

Wen Z Y, Jiang Y, Chen F. High cell density culture of the diatom *Nitzschia laevis* for eicosapentaenoic acid production: fed-batch development. Process Biochem 2002; 37: 1447–1453.

Yamane Y I, Higashida K, Nakashimada Y, Kakizono T, Nisho N. Influence of oxygen and glucose on primary metabolism and astaxanthin production by *Phaffia rhodozyma* in batch and fed-batch culture: kinetic and stoichiometric analysis. Environ Microbiol 1997; 63: 4471–4478.

Yuan J P, Chen F, Liu X, Li X Z. Carotenoid composition in the green microalga *Chlorococcum*. Food Chem 2002; 76: 319–325.

Zaslavskaia L A, Lippmeier J C, Shih C, Ehrhardt D, Grossman A R, Apt K E. Tropic conversion of an obligate photoautotrophic organism through metabolic engineering. Science 2001; 292: 2073–2075.

Zhang D H, Lee Y K. Two-step process for keto-carotenoid production by a green alga, *Chlorococcum* sp. strain MA-1. Appl Microbiol Biotechnol 2001; 55: 537–540.

What is claimed is:

1. A method of producing astaxanthin comprising cultivating a green microalga *Chlorella* in the dark in a medium having a carbon:nitrogen weight ratio of at least about 18, and recovering astaxanthin therefrom.

2. The method of claim 1 in which the medium has a carbon:nitrogen weight ratio of at least 18.

3. The method of claim 2 in which the *Chlorella* is *Chlorella zofingiensis*.

4. The method of claim 3 wherein the medium contains glucose.

5. The method of claim 2 further comprising adding a carbon source to a medium to achieve said carbon:nitrogen weight ratio.

6. The method of claim 5 in which the carbon source added is glucose.

7. The method of claim 1 in which the *Chlorella* is *Chlorella zofingiensis*.

8. The method of claim 7 wherein the medium contains glucose.

9. The method of claim 1 further comprising adding a carbon source to a medium to achieve said carbon:nitrogen weight ratio.

10. The method of claim 9 in which the carbon source added is glucose.

11. In a method of cultivating a green microalga *Chlorella* on media in a dark-heterotrophic culture, the improvement which comprises effecting the culture on a medium having a carbon:nitrogen weight ratio of at least about 18, and recovering astaxanthin therefrom.

12. The method of claim 11, in which the carbon:nitrogen weight ratio is at least 18.

13. The method of claim 12, in which the green microalga *Chlorella* is *Chlorella zofingiensis*.

14. The method of claim 13, in which the medium contains glucose.

15. The method of claim 11, in which the green microalga *Chlorella* is *Chlorella zofingiensis*.

16. The method of claim 15, in which the medium contains glucose.

* * * * *